United States Patent [19]
Hartt

[11] Patent Number: 5,426,973
[45] Date of Patent: Jun. 27, 1995

[54] METHODS FOR DETECTION AND PREVENTION OF CONCRETE CRACKING AND SPALLING ASSOCIATED WITH EMBEDDED METAL CORROSION

[75] Inventor: William H. Hartt, Boca Raton, Fla.

[73] Assignee: Florida Atlantic University, Boca Raton, Fla.

[21] Appl. No.: 874,459

[22] Filed: Apr. 24, 1992

[51] Int. Cl.$^6$ .................. G01N 17/00; G01N 33/38
[52] U.S. Cl. ............................. 73/86; 73/762; 106/640
[58] Field of Search .............. 106/643, 644, 640; 73/86, 149, 762, 787

[56] References Cited

U.S. PATENT DOCUMENTS

| | | | |
|---|---|---|---|
| 3,595,072 | 7/1971 | Richards | 73/803 |
| 3,732,725 | 5/1973 | Allen, Jr. | 73/81 |
| 4,139,814 | 2/1979 | Radd et al. | 73/86 |
| 4,365,999 | 12/1982 | Fujita et al. | 106/644 |
| 4,524,604 | 6/1985 | Vondran | 73/38 |
| 4,915,910 | 4/1990 | Manning et al. | 73/865.6 |
| 4,961,790 | 10/1990 | Smith et al. | 106/823 |
| 5,127,954 | 7/1992 | Johnston et al. | 106/644 |
| 5,219,388 | 6/1993 | Meletiou et al. | 73/155 |
| 5,365,779 | 11/1994 | Velde | 73/86 |

OTHER PUBLICATIONS

"Highway and Bridge Needs: 1987–2005," Chapter IV in *The Status of the Nation's Highways and Bridges: Conditions and Performance and Highway Bridge Replacement and Rehabilitation Program* 1989, Report of the Secretary of Transportation to the United States Congress, U.S. Government Printing Office, Washington, Jun. 1989.

Grimes, W. D., W. H. Hartt, D. H. Turner (1979) "Cracking of Concrete in Sea Water Due to Embedded Metal Corrosion," Corrosion 35:309 (no month).

Raharinaivo, A., J.-M. R. Genin "On the corrosion of reinforcing steels in concrete in the presence of chlorides," *Materiales de Construccion*, 36(4):5–16 (Oct. 1986).

Clear, K. C., Y. P. Virmani "Solving Rebar Corrosion Problems in Concrete Research Update: Methods and Materials," Paper No. 4, Proceedings of Seminar on Solving Rebar Corrosion Problems in Concrete, Natl. Assn. Cor. Engrs. (Sep. 1982).

Slater, J. E. (1983) *Corrosion of Metals in Association with Concrete*, STP 818, Am. Soc. for Test. and Matls., Phila., pp. 1–9 (no month).

Piling, N., R. Bedworth (1923) "The oxidation of metals at high temperatures," *J. Inst. of Metals* 29:534 (no month).

Primary Examiner—Anthony J. Green
Attorney, Agent, or Firm—Saliwanchik & Saliwanchik

[57] ABSTRACT

Applicant has discovered a new mechanism which induces the cracking and spalling of metal-reinforced concrete. Methods and compositions for preventing such cracking and spalling are provided. Methods of testing compositions or admixtures for effectiveness in preventing cracking and spalling are also provided.

5 Claims, 3 Drawing Sheets

METHODS FOR DETECTION AND PREVENTION OF CONCRETE CRACKING AND SPALLING ASSOCIATED WITH EMBEDDED METAL CORROSION

BACKGROUND OF THE INVENTION

Reinforced concrete is a widely-accepted material of construction. Within the past 30 years, severe deterioration of many reinforced concrete structures has been observed with increasing frequency throughout the United States. Over an approximately 5-year period, the Federal Highway Administration adjusted its estimate of repair costs due to concrete deterioration in transportation systems alone from $50 billion to $700 billion ("The Status of the Nation's Highways and Bridges: Conditions and Performance and Highway Bridge Replacement and Rehabilitation Program 1989," Report of the Secretary of Transportation to the United States Congress, U.S. Government Printing Office, Washington, June 1989). This problem is widespread, affecting not only transportation infrastructure components, but also "snowbelt" structures, as well as coastal buildings and related structures. The safety and longevity of such reinforced concrete structures are prime concerns, and methods of protection are therefore important.

The basic problem associated with the deterioration of conventional reinforced concrete due to corrosion of embedded reinforcement is generally not that the reinforcing material itself is reduced in mechanical strength, but rather that the concrete cracks. Until now, it has been assumed that the products of corrosion exert stresses within the concrete which cannot be supported by the limited plastic deformation of the concrete, and therefore cracking of the concrete occurs. This was based on the erroneous assumption that the corrosion products from the steel occupy a relatively high specific volume within the concrete matrix and that this causes tensile stresses which lead to concrete cracking and spalling.

Cracking of concrete can lead to problems regarding structural soundness (on, for example, pilings), to discomfort (for example, chuckholes in bridges), or to cosmetic problems (as in the case of facades on buildings). Since concrete that has reached this state of deterioration is frequently extremely difficult to rehabilitate, significant effort has been expended to develop techniques capable of detecting the corrosion at an earlier stage.

Concrete contains pores which are interconnected throughout it, and this extensive network leads to permeability of the concrete to both liquids and gases. This is of critical importance in the corrosion process, because both the initiators (generally, chloride ion) and supporters (for example, oxygen) of corrosion of the reinforcing steel must diffuse through the overlying concrete to the steel.

A major influence that the composition of concrete exerts on the environment of any reinforcing steel which is placed within it is a relatively high pH. The pH appears to be governed by the free sodium, potassium, and calcium hydroxides within the concrete, which gives a pH somewhat above 12. There have been suggestions that the ultimate agent governing pH is, in fact, alkali content of the cement, because the pH of a saturated calcium hydroxide solution (pH 12.6) is lower than that observed from concrete pore water which has been "squeezed out" of hardened cement, mortar, and concrete.

It is believed in the art that various combinations of, and interactions between, geothite ($\alpha$-FeOOH), magnetite ($Fe_3O_4$), lepidocrocite ($\gamma$-(8FeOOH,FeOCl)), and hydroxides and chloride containing hydroxides ($2Fe(OH)_2 \cdot FeOHCl \cdot Fe(OH)_2Cl$) comprise the species at or near the embedded metal surface, with the relative amount of each varying with $Cl^-/OH^-$ and temperature. Upon exposure to air and complete oxidation, iron reacts to $Fe(OH)_3$ or $Fe_2O_3$. Experiments in which $Ca(OH)_2$ solutions were titrated with $FeCl_2$, and in which pH versus time was maintained for similar solutions of differing $Cl^-/OH^-$ ratios, have reproduced the actual pH transition that occurs in concrete or mortar (Grimes, W. D., W. H. Hartt, D. H. Turner [1979] *Corrosion* 35:309; Raharinaivo, A., J.-M.R. Genin [1986]*Materiales de Construccion*, Vol. 36, Oct., Nov., Dec., p. 5; Clear, K. C., Y. P. Virmani [1983] "Solving Rebar Corrosion Problems in Concrete Research Update: Methods and Materials," Paper No. 4, Proceedings of Seminar on Solving Rebar Corrosion Problems in Concrete, Natl. Assn. Cor. Engrs.).

Grimes et al. (Grimes et al [1979] supra) and Slater (Slater, J. E. [1983] *Corrosion of Metals in Association with Concrete*, STP 818, Am. Soc. for Test. and Matls., Phila., p. 5) have rationalized the tendency for solid corrosion products to crack concrete to the protectiveness of oxides formed during high temperature treatment, as quantified historically by the Piling-Bedworth ratio (Piling, N., R. Bedworth [1923] *J. Inst. of Metals* 29:534). On this basis, the specific volume of the oxide is compared to that of the metal from which it is formed, with oxide spalling tendency (reduced protectiveness) increasing in proportion to the ratio of the volumes (oxide-to-metal).

Certain additives have been used in attempts to improve the performance of reinforced concrete. Latex-modified concrete essentially uses a polymer emulsion in the mix-water which apparently impedes the penetration of surface chlorides into the concrete (and possibly oxygen diffusion through the concrete as well). Incorporation of wax compounds has also been used to create "internally sealed" concrete. In this approach, a heating cycle is employed following curing of the cement to came a hydrophobic layer of wax to form on the pore walls, which prevents ingress of surface chemicals.

The foregoing attempts, however, are directed to preventing the corrosion of embedded steel. These are in response to the view that accumulation of corrosion product in the concrete pore space produces tensile hoop stresses and, ultimately, cracking and spalling. There have been virtually no experimental results contradicting this proposed mechanism, the corrosion product/mechanical pressure (CPMP) cracking mechanism, in the past 80 years; and very little data has been developed to provide confirmation of the CPMP cracking mechanism. In contrast, the subject invention focuses on a different mechanism of concrete cracking and spalling from that which has been accepted for most of this century.

BRIEF SUMMARY OF THE INVENTION

The subject invention results from the discovery that a fundamental feature of the mechanism whereby concrete cracks has previously gone unrecognized. We have found that cement wetting by soluble corrosion products causes differential volume cement cracking (the DVCC mechanism), and this plays a significant role in the cracking and spalling of concrete. The subject invention comprises treatments and admixtures which prevent, or greatly reduce, the expansion due to corrosion product wetting, thereby prolonging the time between hardening of the concrete, and onset of concrete cracking.

The subject invention is a new mitigation strategy which prevents or minimizes the relatively high level of wetting induced cement expansion in association with acidic corrosion products, a unique approach to preventing concrete cracking and spalling.

Experiments consisting of exposure of hardened cement paste and concrete specimens to deaerated ferrous chloride solutions revealed (a) an abnormally large expansion in solutions with pH in the approximate range 2–4, and (b) network cracking of specimens exposed to approximately this same pH range. The information provided by these experimental results shows that the mechanism of concrete cracking involves a cement expansion induced by wetting by soluble corrosion product. The ferrous chloride in the experiments described above simulated the corrosion products which form in actual cement, mortar, or concrete. Correspondingly, according to the subject invention, corrosion induced concrete cracking can be reduced or eliminated by cement compositions or concrete additions which minimize this expansion. This is a unique idea which is wholly unaddressed in the technical literature.

The subject invention further comprises procedures for testing concrete treatments and admixtures to determine whether they will prevent, or are likely to help prevent, concrete cracking and spalling induced by the DVCC mechanism.

DETAILED DESCRIPTION OF THE INVENTION

Figure 1:
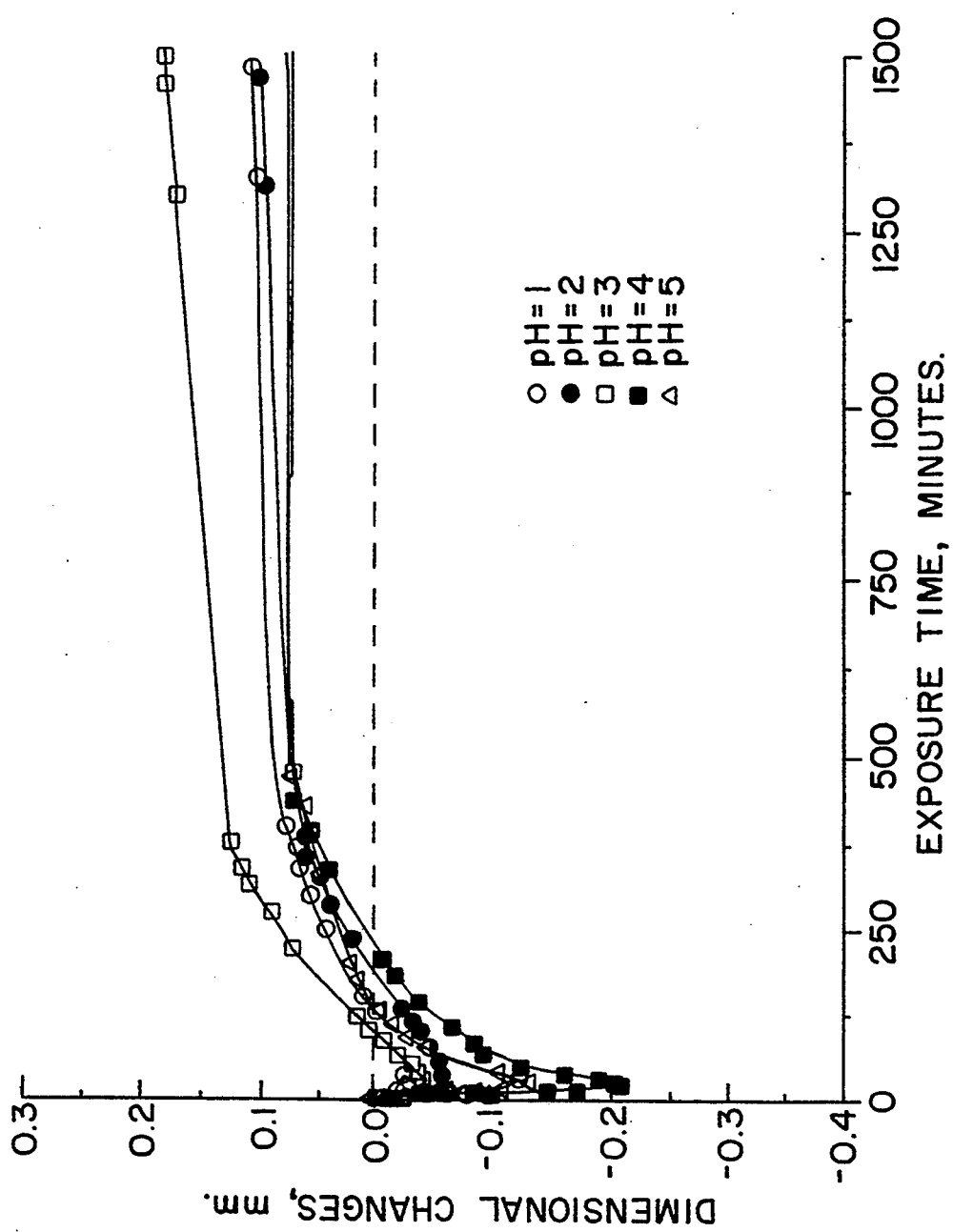
FIG. 1 presents dimensional changes versus exposure time data for cement paste specimens, immersed in solutions of pH from 1–5.

Concrete cracking as a consequence of embedded metal corrosion presently constitutes the single most costly corrosion problem in this country, with an annual price tag of multi-billions of dollars. Deterioration of this material class was first recognized shortly after the turn of the century, and a number of mechanisms were proposed as explanations. Questions regarding the mechanism of this attack were considered resolved in 1913 when NBS issued a comprehensive report of research findings which concluded that the deterioration was a consequence of accumulation in the cement or concrete pore structure near corroding, embedded steel of reaction products which have greater specific volume than the metal from which they are formed. Consequently, internal stresses were believed produced which ultimately caused cracks. This explanation for concrete distress in association with embedded metal corrosion has been universally accepted ever since and has never been seriously questioned or challenged.

The subject invention concerns the discovery of an alternative mechanism of concrete cracking in association with embedded metal corrosion. In the discovery of the subject invention, experiments were conducted which involved measurement of the volumetric change of hardened cement and concrete specimens upon exposure to simulated pore water solutions containing soluble iron corrosion products, notably ferrous chloride. Previous research has measured the pH of corrosion products in concrete adjacent to embedded steel and found this to be approximately 3–5, suggesting that these can be simulated by a deaerated $FeCl_2$ solution. This was done for a range of pH from 1 to 13, the latter being comparable to that for normal cement or concrete pore water. We discovered relatively large volumetric expansion of the cement and concrete specimens occurred upon exposure to solutions of pH near 3.5. The magnitude of the expansion difference between specimens exposed to this pH range compared to ones exposed to solutions without simulated corrosion products showed that locations of iron corrosion products in actual concrete expand sufficiently to cause cracks in adjacent (unexpanded) regions where corrosion products are not present. Particularly noteworthy is the observation that specimens exposed in solutions of pH near that for iron corrosion products in concrete developed a network of cracks throughout the material despite the fact that no external stress was applied. Specimens in more acidic solutions developed few, if any, cracks; and those in higher pH solutions did not crack at all.

These results can be explained in terms of an expansion induced by wetting by soluble corrosion products within the submicroscopic cement gel particles, the magnitude of which is relatively large in the range of pH exhibited by soluble iron corrosion products.

We believe that the mechanism for concrete cracking involves the following steps:

1. Penetration of chlorides into concrete.
2. Localized depassivation and active corrosion of embedded steel once chloride concentration becomes sufficiently high.
3. Accumulation in the concrete pore space adjacent to actively corroding steel of $FeCl_2$ and other products which reduce the pH locally.
3. Expansion of the cement particles that are wetted by the acid corrosion products and development of tensile stresses which leads to cracking in adjacent (unwetted and unexpanded) cement and concrete.

The implications of a cement wetting induced expansion mechanism are profound. Previously, the only recognized technique for stopping corrosion induced cracking was to reduce or stop the corrosion. While this technique can still be used, it should be equally effective in preventing cracking to reduce the hydration expansion, in particular the relatively large expansion which occurs in association with soluble corrosion products. One aspect of the subject invention concerns products, admixtures, and formulations which reduce or eliminate this expansion.

Following are examples which illustrate procedures, including the best mode, for practicing the invention. These examples should not be construed as limiting. All percentages are by weight and all solvent mixture proportions are by volume unless otherwise noted.

EXAMPLE 1

Pangrazzi et al. (Pangrazzi, R., W. H. Hartt [1991] "An Analysis of Strain Changes in Cathodically Polarized Pretensioned Concrete Specimens," Paper No. 554 presented at CORROSION/91, Cincinnati, Mar. 11–15, 1991) recently reported the results of experiments on pretensioned concrete specimens from monitoring of shape changes via strain gauges mounted upon the exterior concrete surface during laboratory air and seawater exposure. The seawater exposure involved different combinations of free corrosion and anodic and cathodic polarization. The strain increase over time reflected an expansion of the concrete which is consistent with loss of bond. However, comparison of the observed expansion with results of an analytical evaluation which projected quantitatively the elongation that should occur from even complete loss of bond revealed that the former exceeded the latter by as much as an order-of-magnitude. Thus, the conclusion that, while loss of bond may have contributed to the concrete expansion, another factor (or factors) was responsible for the bulk of the shape change. We have discovered that the cause is a relatively pronounced cement expansion induced by wetting in association with acidic reaction products.

Figure 2:
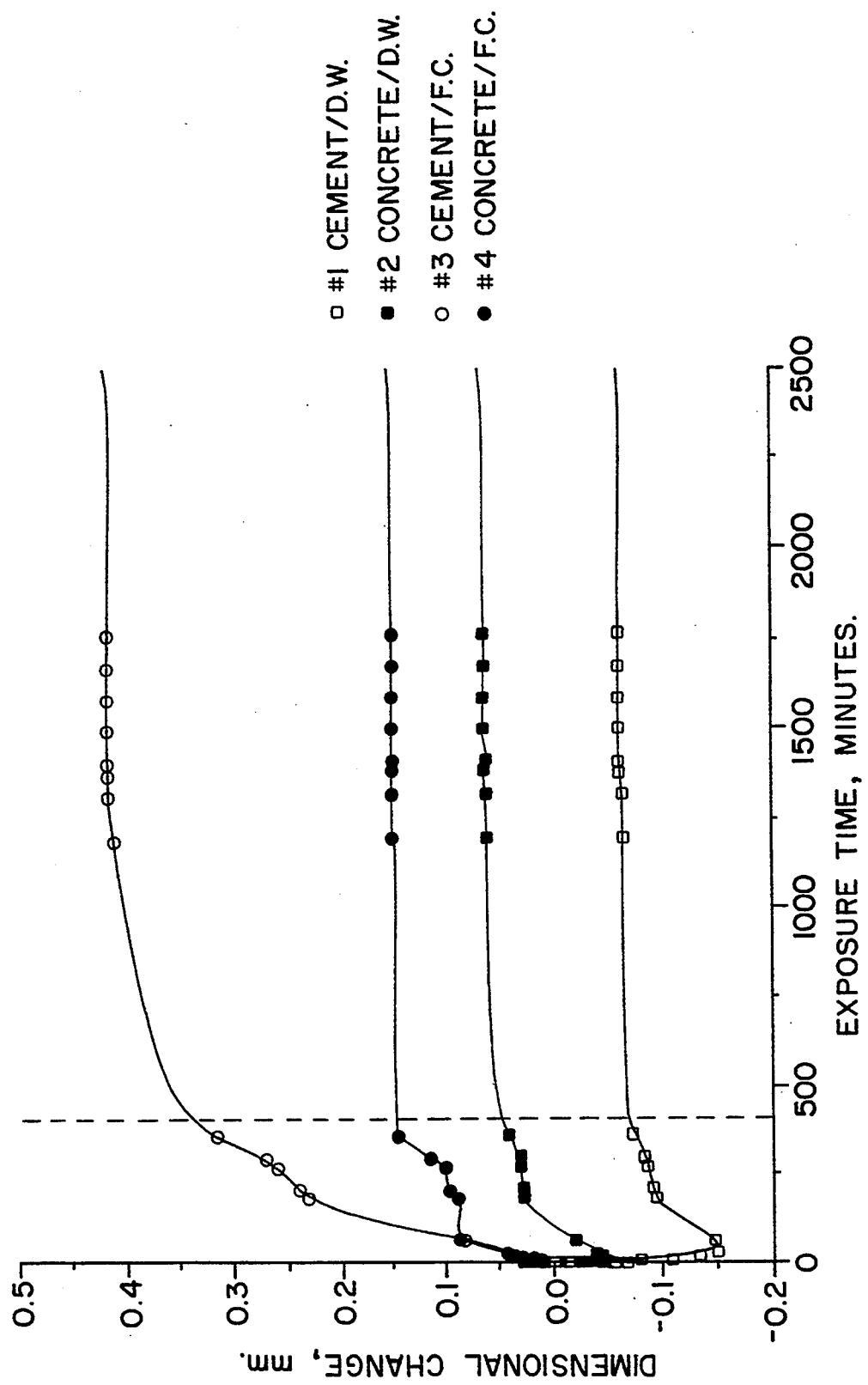
FIG. 2 presents dimensional changes versus exposure time data for concrete and cement paste specimens exposed to ferrous chloride and distilled water solutions.

Experiments have been performed upon 100 mm diameter by 13 mm thick concrete and cement paste cylinders which were instrumented with an extensometer and exposed to deaerated solutions of different pH ranging from that expected for normal pore water ($\approx 13$ or higher) to below that which should occur at anodic sites on embedded steel (pH$\approx$4). The concrete cylinders were obtained by slicing cores from the pretensioned beams referenced above, while the cement paste ones were cast within PVC rings utilizing a mix with water/cement of 0.50. Acid solutions were comprised of $FeCl_2$ in distilled water and the alkaline of KOH—NaOH—$Ca(OH)_2$ solutions. A strain gauge instrumented stainless steel strip was attached by Teflon holders to the cylinders and was employed to monitor shape change. This strip was pre- and post-test calibrated by a linear displacement device with $10^{-2}$ mm resolution. FIGS. 1 and 2 present dimensional change versus exposure time data for concrete and cement paste specimens immersed in different solutions. The results demonstrate, first, greater expansion for the cement paste than for the concrete and, second, relatively large expansion in the low pH regime. The former is attributed to the larger percentage of cement in the paste versus the concrete specimen. The important point demonstrated here is the surprising expansive nature of the acid exposed specimens compared to those in the neutral or basic solutions.

In a subsequent experiment a mortar specimen was heated to 95° C. for ten hours and then exposed to deaerated $FeCl_2$ (initial pH=3.9). Audible ticking occurred during this exposure, and post-test visual and microscopic inspection revealed both macroscopic and networks of microscopic cracks. The specimen was fractured with relative ease, and the depth of rust staining after air exposure was 2–3 mm.

Figure 3:
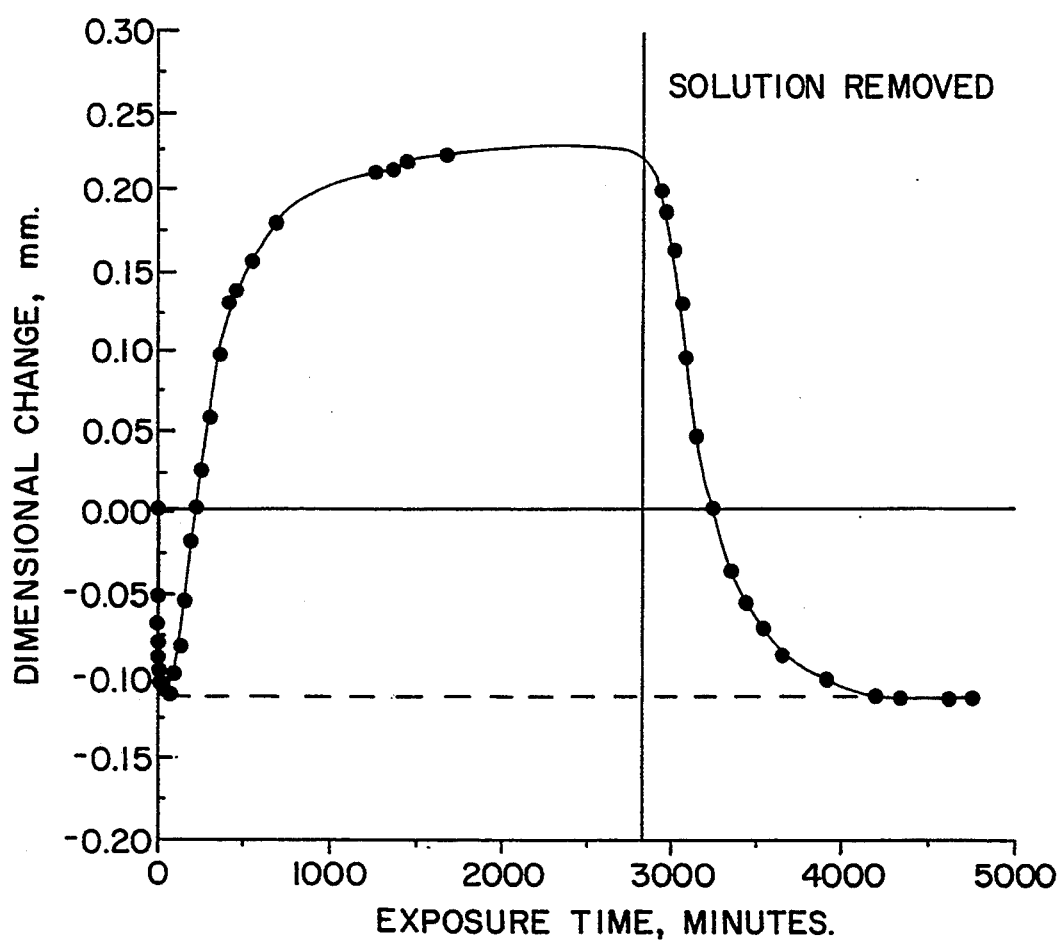
FIG. 3 reports expansion measurements on a specimen that was initially dried at 95° C., wetted with deaerated $FeCl_2$ (pH=3) for 2800 minutes and subsequently dried in laboratory air.

None of the experimental results presented necessarily contradicts or renders invalid the CPMP model of concrete cracking due to embedded metal corrosion. However, the fact that the concrete pore solution at anodic sites on embedded steel is acidic (pH$\approx$4) and that cement wetting by this low pH electrolyte results in a relatively large specific volume increase for this phase suggest that this mechanism alone, or in concert with the CPMP process, causes cracking. FIG. 3 reports expansion measurements on a specimen that was initially dried at 95° C., wetted with deaerated $FeCl_2$ (pH=3) for 2800 minutes and subsequently dried in laboratory air. As shown in the figure, the long-term specimen dimension (after drying) was the same as for the short-term minimum. This experiment proves the fact of hydration-induced cement expansion, as the specimen would not have contracted upon drying if precipitation of a solid product(s) had been responsible for the expansion.

It is possible for different types of additives to concrete, or even for different types of concrete themselves, to register different pH values.

EXAMPLE 2

Magnitude and pH Dependence of CHE

At actively corroding sites on an embedded steel surface (no impressed current), pH is about 4, and a pH gradient is established with distance into the mortar or concrete as controlled by outward diffusion of $Fe^{++}$ and $H^+$ and inward migration of $Cl^-$ and $OH^-$. The stress developed at such locations can be determined by the differential expansion between the high and low pH regions, the distance over which this takes place, and the volume of the more expanded material.

This can be observed by exposing thin (thickness 0.5 mm or less) cement, mortar, and concrete specimens to relatively large, stirred volumes of deaerated simulated pore water (solutions of NaOH, KOH, and $Ca(OH)_2$) with various $FeCl_2$ additions. Hydration induced expansion can be monitored utilizing a custom designed extensometer based upon the principle of the one disclosed in Example 1, but modified to accommodate this experiment's more fragile specimen. This thinner specimen facilitates more uniform solution absorption through the cross section with minimal pH modification. Some specimens can be dried prior to exposure by either heating to 95° C. or evacuation. Consequently, the expansion can be characterized as a function of pH. Bulk solution pH can be monitored in situ during the experiment, and pore water pH can be measured after exposure according to documented procedures. These experiments can be performed utilizing different cement types (normal Portland, low heat of hydration, sulfate resistant, fly ash, silica fume, and modifications of these), different water-cement ratio (0.35–0.60) and a range of temperatures in the ambient range (0°–40° C.), thereby correlating wetting expansion with cement chemistry, mix design, and exposure variables. Therefore, these experiments provide a means of testing various cement and concrete formulations, including various admixtures or treatments, to determine whether such formulations, admixtures, or treatments are effective in preventing or reducing the effects of cement wetting expansion.

EXAMPLE 3

Relevance of Cement Wetting Expansion Cracking

Experiments can be performed to measure the pH and the pH gradient extending from locations of active corrosion in actual reinforced concrete specimens which have been part of different research programs at the Center for Marine Materials over the last 15 years. This can involve breaking of specimens, treatment of corroded areas with different pH indicators, and examination by low level microscopy. Next, one can model the strains and stresses which occur in association with differential wetting expansion. This can be accomplished by finite element analysis (FIEA), which permits quantification of the various parameters (pH differential and gradient) which cause strains capable of cracking concrete or mortar. The FEA results can then be compared to tensile strengths for mortar and concrete. In this manner the process (wetting-induced expansion of concrete/mortar cracking) can be modeled.

EXAMPLE 4

Reevaluation of the Corrosion Product/Mechanical Pressure (CPMP) Mechanism

To understand the relative importance of the DVCC and CPMP mechanisms, a series of experiments can be performed involving simulated pore water solution and monitoring of the evolution of corrosion products through the various oxidation stages. The procedure is based upon a deaerated, simulated pore solution which is closed except for access through different graduated pipettes. Initially, a known amount of ferrous chloride can be introduced and the solution volume change monitored as a function of time via rise and fall in one of the pipettes. Subsequently, a known amount of oxygen can be introduced and any volume changes associated with oxidation monitored. The final product will be Fe(OH)$_3$ or Fe$_2$O$_3$ or a hydrated form thereof. Relevance of CPMP to corrosion induced concrete cracking would be evaluated based upon the magnitude of any specific volume increase in association with corrosion product evolution. The relative contribution of CPMP compared to DVCC can be based upon an analysis of the strains that would be induced in the cement, mortar, or concrete pore space by each. These experiments and analyses confirm that DVCC is a significant contributor to concrete and mortar cracking.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A method of testing concrete, cement, or mortar which is to be metal reinforced for susceptibility to cracking or spalling, said method comprising:

exposing a thin layer of the concrete, cement, or mortar to a ferrous chloride solution having a pH of 2 to about 4, wherein said solution is provided in an amount whereby the thin layer of concrete, cement, or mortar becomes wetted; and monitoring expansion of the concrete, cement, or mortar.

2. The method, according to claim 1, wherein said concrete, cement, or mortar layer is about 13 mm or less in thickness.

3. The method, according to claim 1, wherein said concrete, cement, or mortar layer is about 0.5 mm or less.

4. The method, according to claim 1, wherein said solution further comprises an alkaline component, said alkaline component being selected from the group consisting of NaOH, KOH, and Ca(OH)$_2$.

5. The method, according to claim 1, wherein said monitoring of expansion is conducted using an extensometer.

* * * * *

UNITED STATES PATENT AND TRADEMARK OFFICE
CERTIFICATE OF CORRECTION

PATENT NO. : 5,426,973
DATED : June 27, 1995
INVENTOR(S) : William H. Hartt

It is certified that error appears in the above-indentified patent and that said Letters Patent is hereby corrected as shown below:

Column 2, lines 45-46: Delete "to came a" and insert --to cause a--.

Column 7, line 4: Delete "(FIEA)" and insert --(FEA)--.

Signed and Sealed this

Twenty-sixth Day of September, 1995

Attest:

BRUCE LEHMAN

*Attesting Officer*   Commissioner of Patents and Trademarks